(12) United States Patent
Wei et al.

(10) Patent No.: US 7,389,703 B2
(45) Date of Patent: Jun. 24, 2008

(54) SAMPLER FOR ENGINE EXHAUST DILUTION

(75) Inventors: Qiang Wei, Novi, MI (US); Ichiro Asano, Konan (JP)

(73) Assignee: Horiba Instruments, Inc., Irvine, CA (US)

( * ) Notice: Subject to any disclaimer, the term of this patent is extended or adjusted under 35 U.S.C. 154(b) by 331 days.

(21) Appl. No.: 11/239,268

(22) Filed: Sep. 29, 2005

(65) Prior Publication Data

US 2007/0068236 A1    Mar. 29, 2007

(51) Int. Cl.
*G01N 1/24* (2006.01)
(52) U.S. Cl. .................................... 73/863.03
(58) Field of Classification Search .............. None
See application file for complete search history.

(56) References Cited

U.S. PATENT DOCUMENTS

| | | | |
|---|---|---|---|
| 3,975,953 A | 8/1976 | Smith et al. | |
| 4,586,367 A | 5/1986 | Lewis | |
| 5,058,440 A | 10/1991 | Graze, Jr. | |
| 5,090,258 A | 2/1992 | Yamasaki et al. | |
| 5,756,360 A | 5/1998 | Harvey et al. | |
| 6,016,711 A | 1/2000 | Ullman et al. | |
| 6,062,092 A | 5/2000 | Weaver | |
| 6,200,819 B1 | 3/2001 | Harvey et al. | |
| 6,460,400 B1* | 10/2002 | Ichikawa | 73/23.31 |
| 6,546,812 B2* | 4/2003 | Lewis | 73/861.63 |
| 6,615,677 B2 | 9/2003 | Dickson et al. | |
| 6,729,195 B2 | 5/2004 | Graze, Jr. | |
| 2005/0160838 A1* | 7/2005 | Weaver | 73/863.03 |

* cited by examiner

*Primary Examiner*—Robert R Raevis
(74) *Attorney, Agent, or Firm*—Brooks Kushman P.C.

(57) ABSTRACT

A partial flow sampling system includes a system inlet for receiving an exhaust sample flow from a sample inlet probe and transfer line. The system further includes a dilution air control system for controlling a dilution air flow rate, and a mixer. The mixer receives and mixes the exhaust sample flow and the dilution air flow to produce a mixture flow. A total flow control system controls the mixture flow rate. An orifice flow meter installed at the system inlet measures the exhaust sample flow rate in. real-time. This provides accurate sample flow measurements over a wide range of dilution ratios and sample ratios.

10 Claims, 3 Drawing Sheets

SAMPLER FOR ENGINE EXHAUST DILUTION

BACKGROUND OF THE INVENTION

1. Field of the Invention

The invention relates to a sampler for taking a sample from raw engine or vehicle exhaust, or from a primary dilution system.

2. Background Art

The United States Environmental Protection Agency (EPA) defines engine emitted particulate matter (PM) as material collected by filtration of diluted exhaust with a filter temperature of not more than 52° C. A large number of dilution systems have been developed to meet this criterion.

The constant volume sampler (CVS) is a full flow dilution tunnel. The CVS takes all engine exhaust and dilutes the exhaust proportionally. The dilution process in the CVS is straightforward, and is very accurate for gaseous and PM measurement. However, the CVS is expensive, large in size, and not portable. As well, a specific CVS may only be used for a particular range of engine sizes.

Another approach to diluting engine exhaust is provided by the partial flow sampling system. The partial flow sampling system takes a small fraction of flow from the engine exhaust. In comparison to the CVS, the partial flow sampling system has advantages such as being relatively inexpensive, having a smaller size, as well as being useable for any size of engine, etc. Due to the nature of the dilution process, a complicated control system must be integrated for proportional control during transient testing conditions. Additional information, such as real-time engine exhaust flow rate, needs to be provided for dilution control during the transient testing conditions.

The conventional partial flow sampling system controls dilution air flow and total flow. The total flow is defined as the mixture of the dilution air and the sample flow. The difference of the total flow and dilution air flow is the sample flow rate. The following equations define the sample flow, the dilution ratio, and the sample ratio at time $t_i$:

$$Q_{sample\_i} = Q_{total\_i} - Q_{dilutionair\_i}$$

$$Dr_i = \frac{Q_{total\_i}}{Q_{sample\_i}}$$

$$r_i = \frac{Q_{sample\_i}}{Q_{exhaust\_i}} * 100$$

where, $Q_{sample\_i}$ is the sample flow rate into the partial flow sampling system at standard or reference conditions, $Q_{total\_i}$ is the total flow rate at the standard or reference conditions, $Q_{dilutionair\_i}$ is the dilution air flow rate at the standard or reference conditions, $Dr_i$ is the dilution ratio, and $r_i$ is the sample ratio.

When the sample ratio r and the total flow $Q_{total}$ are constant in the partial flow sampling system, the partial flow sampling system simulates the constant volume sampler (CVS) by operating with proportional control. In this situation, more sample flow is taken when exhaust flow rate is higher, and less sample flow is taken when exhaust flow rate is lower. As well, the partial flow sampling system may be operated at constant dilution ratio when the system takes constant exhaust flow and the total flow remains constant.

In the conventional partial flow sampling system, the sample flow rate is obtained from the difference between the total flow and the dilution air flow. Accordingly, significant errors in the sample flow may be generated when the sample flow is small, in other words, when the dilution ratio is high or the sample ratio is low. In this way, small errors in total flow and dilution air flow may result in large errors in the sample flow. As a result, the accuracy of the dilution ratio or the sample ratio decreases when the dilution system runs under high dilution ratio or low sample ratio. The control on the dilution ratio or the sample ratio drifts. This eventually influences the accuracy of the PM measurement.

As discussed above, the accuracy of the sample flow rate ($Q_{sample\_i}$) strongly influences the accuracy of the dilution ratio and sample ratio. As a result, the PM number and mass measurement are influenced. Based on the working principle of the conventional partial flow sampling system, the conventional partial flow sampling system cannot avoid significant errors on the sample flow rate under some conditions.

For the foregoing reasons, there is a need for a sampler for engine exhaust dilution that provides accurate sample flow measurements over a wide range of dilution ratios and sample ratios, thereby providing more accurate results for PM number and mass measurements.

SUMMARY OF THE INVENTION

It is an object of the invention to provide an improved sampler for engine exhaust dilution that provides accurate sample flow measurements over a wide range of dilution ratios and sample ratios. An improved system of the invention provides accurate dilution for engine exhaust PM measurement based on number and mass. In preferred implementations, the sampler may be used on any size engine or vehicle, and is suitable for steady-state and transient tests. Further, an improved partial flow sampling system of the invention may be portable, and relatively inexpensive when compared to a full flow dilution system.

In carrying out the invention, a sampler for engine exhaust dilution is provided. The sampler comprises a dilution air control system, a total flow control system, a mixer, an orifice flow meter, and a sample inlet probe and transfer line. The orifice flow meter is installed at the inlet of the sampler, and measures sample flow rate in real-time. As a result, more accurate sample flow measurements may be obtained. Preferably, the orifice flow meter has high penetration for engine exhaust particles such that the particle losses over the orifice flow meter are negligible.

At a more detailed level, the invention comprehends integrating a PID control loop in the system. In embodiments of the invention that utilize the PID control loop, constant or variable dilution ratio and sample ratio may be obtained. In these implementations, the PID loop controls dilution ratio or sample ratio such that the dilution ratio or sample ratio tracks an expected/reference value by adjusting the dilution air flow rate.

In accordance with the invention, the sampler may provide samples for particle instruments and/or filter measurement. If required, the sampler may provide samples for particle instruments and filter measurement simultaneously.

The advantages associated with embodiments of the invention are numerous. For example, because the sample flow is measured by the orifice flow meter in real-time, accurate dilution ratio and sample ratio are available over a wide range of dilution and sample ratios. As a result, the PM results based on the mass and number are more accurate than in a conventional partial flow sampling system.

DETAILED DESCRIPTION OF THE PREFERRED EMBODIMENTS

Figure 1:
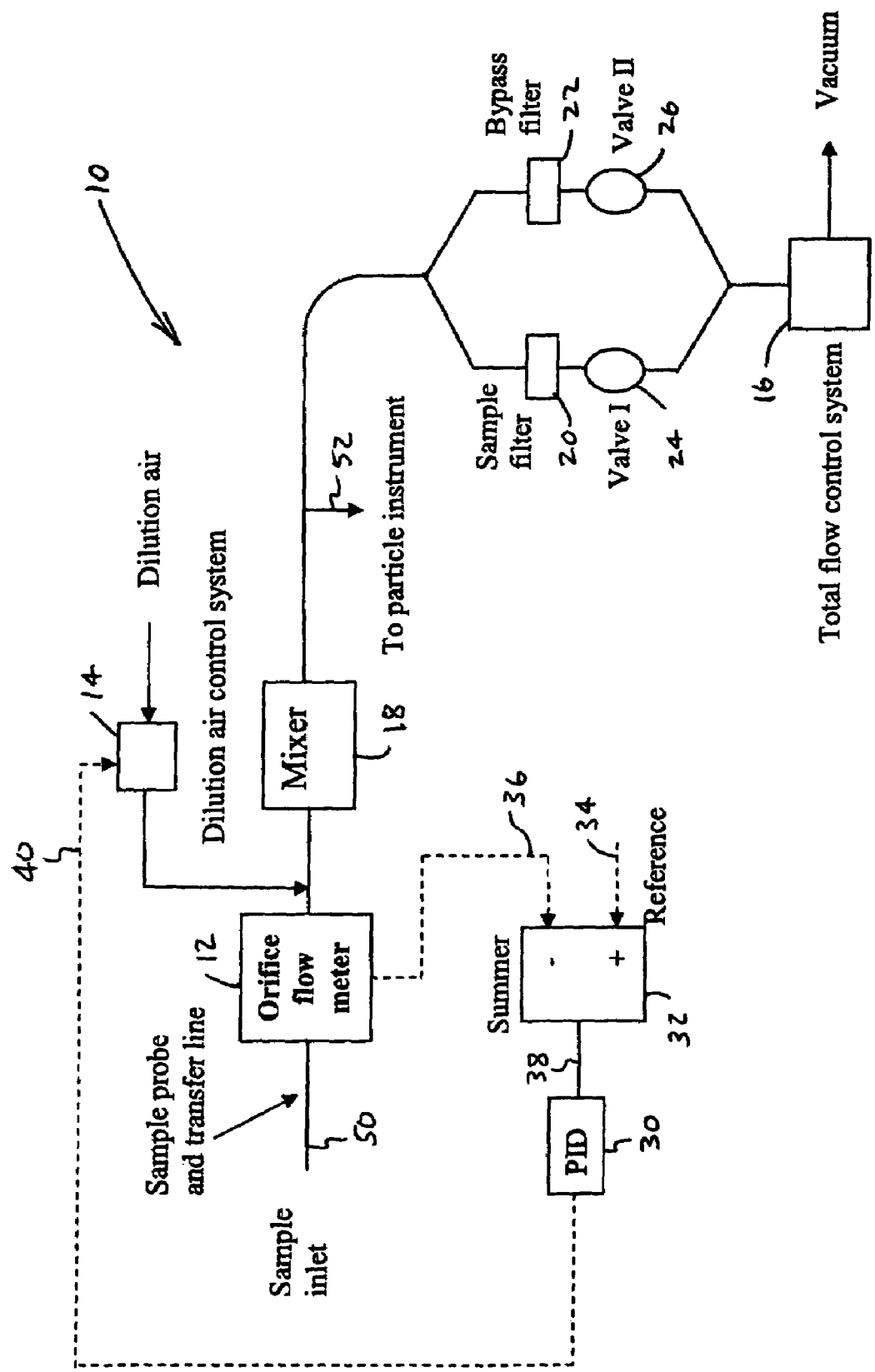
FIG. 1 illustrates a sampler in a preferred embodiment of the invention.

In FIG. 1, the sampler is generally indicated at 10. Sampler 10 includes orifice flow meter 12, dilution air control system 14, total flow control system 16, and mixer 18. Sampler 10 further includes sample filter 20 and associated valve 24, as well as bypass filter 22 and associated valve 26. In this preferred embodiment, sampler 10 further includes proporational, integral, derivative (PID) controller 30. Summer 32 receives reference signal 34 at its positive input. Summer 32 receives feedback signal 36 from orifice flow meter 12 at its negative input. The error signal 38 is processed by PID controller 30 to produce signal 40, which drives dilution air control system 14.

With continuing reference to FIG. 1, the sample flows into sampler 10 through the sample probe and transfer line 50. The flow rate of the sample flow is measured in orifice flow meter 12. The sample flow mixes with dilution air in mixer 18. Mixer 18 may be a tunnel or cyclone or other mixing device. In mixer 18, the sample uniformly mixes with the dilution air without substantial particle losses.

In this preferred embodiment, the dilution air is controlled by a mass air flow controller or other flow control device. If particle instruments and filter measurement are operated simultaneously, a small fraction of flow moves into particle instruments through port 52. Most of the mixture flows through either sample filter 20 or bypass filter 22. The purpose of the integrated bypass filter 22 in sampler 10 is to be able to run sampler 10 when the filter measurement for PM is not started or is not required. As a result, total flow control system 16 is protected from the engine exhaust PM, and the pressure in the system may be balanced before the sample filter 20 is switched in.

On sample filter 20 or bypass filter 22, the engine exhaust PM is collected on the filter. Sample filter 20 or bypass filter 22 can be selected by opening the associated valve 24, 26 downstream of the filter. More specifically, sample filter 20 is selected when valve 24 downstream of sample filter 20 is open and the valve 26 downstream of bypass filter 22 is closed. In the opposite way, bypass filter 22 may be selected. The valves may be controlled manually or automatically. Finally, flow moves into total flow control system 16. The total flow, which is the mixture of dilution air and sample flow, is controlled by either a mass flow controller, critical orifice, or other flow control device.

In accordance with this preferred embodiment of the invention, sampler 10 may be operated under three modes. In the first mode, only the particle instrument is running, and the total flow moves through bypass filter 22. In the second mode, only filter measurement is running, and the total flow moves through bypass filter 22 before the filter measurement for PM starts. When the filter measurement for PM starts, the total flow moves through sample filter 20. There is no flow to the particle instrument in this second mode. In the third mode, both particle instrument and filter measurement are running simultaneously. In this third mode, the total flow moves through bypass filter 22 before the filter measurement for PM starts. When the filter measurement for PM starts, the total flow moves through sample filter 20. There is a flow to the particle instrument in this third mode.

The PID loop controls dilution ratio or sample ratio to track expected or desired values. By comparing the sample flow signal 36 from the orifice flow meter 12 to the reference 34 in the summer 32, the dilution air flow is adjusted to obtain expected dilution ratio or sample ratio while the total flow remains constant. The following equations present the calculation of the dilution ratio, sample ratio, total sample flow in sample time t on the sampler at time $t_i$:

$$Dr_i = 1 + \frac{Q_{\text{dilutionair\_i}}}{Q_{\text{Measuredsample\_i}}} \quad (1)$$

$$= \frac{Q_{\text{total\_i}} + Q_{\text{particleinstrument\_i}}}{Q_{\text{Measuredsample\_i}}}$$

$$r_i = \frac{Q_{\text{Measuredsample\_i}}}{Q_{\text{exhaust\_i}}} * 100 \quad (2)$$

$$Q_{\text{totalsample}} = \sum_{i=0}^{N} Q_{\text{Measuredsample\_i}} \cdot \delta t \quad (3)$$

where $Dr_i$ is the dilution ratio, $Q_{dilutionair\_i}$ is the dilution air flow at standard or reference conditions, $Q_{Measuredsample\_i}$ is the measured sample flow by the orifice flow meter at the standard or reference conditions, $Q_{exhaust\_i}$ is the flow rate for engine or vehicle exhaust at the standard or reference conditions, $Q_{totalsample}$ is the total sample flow volume in sample time t at the standard or reference conditions, N is the total sample number, and $\delta t$ is the time interval between two sample points. The total flow that moves through sample filter 20 or bypass filter 22 is $Q_{total\_i}$, which is the total flow controlled by the total flow control system 16. $Q_{particleinstrument\_i}$ is the flow to the particle instruments.

When the total flow, flow to particle instruments, and the expected dilution ratio are known, the expected sample flow rate can be calculated from equation 1. By adjusting dilution air flow, the expected sample flow rate can be achieved. As a result, the expected dilution ratio can be obtained. The dilution ratio could be either a constant or a time varying value. In some cases, the flow to particle instruments could be zero if there are no particle instruments running.

When the total flow, flow to particle instruments, and the expected sample ratio are known, the expected sample flow can be calculated from equation 2. By adjusting dilution air flow, the expected sample flow rate can be achieved. As a result, the expected sample ratio can be obtained. The sample ratio could be either a constant or a time-varying value. In some cases, the flow to particle instruments could be zero if there are no particle instruments running.

When the sample ratio, total flow, and flow to particle instruments are kept as constant, sampler 10 simulates the proportional control of a full flow tunnel such as the CVS.

Orifice flow meter 12 is installed upstream of mixer 18 and close to the sample source. Orifice flow meter 12 measures the sample flow rate in real-time. Orifice flow meter 12 includes appropriate components such as, for example, a thermocouple, orifice, differential pressure transducer, and absolute pressure transducer. When the sample flow is changed, the pressure difference over the orifice is changed as well. The pressure drop (pressure difference) is measured by the differential pressure transducer.

The flow rate through the orifice of orifice flow meter 12 is calibrated as a function of the pressure difference over the orifice at the standard or reference conditions. The calibration curve is generated by a precise flow meter, and expressed as a polynomial or other equation which could express the flow rate over the entire calibration range. At a given pressure difference over the orifice, the flow rate can be calculated with the equation.

During operation, the sample flow temperature and pressure may not be at the standard or reference conditions. An absolute pressure transducer and a thermocouple measure the absolute pressure and temperature of the sample flow, respectively. Then, the sample flow can be corrected to the standard or reference conditions. The corrected sample flow is used to obtain the dilution ratio or sample ratio.

Figure 2:
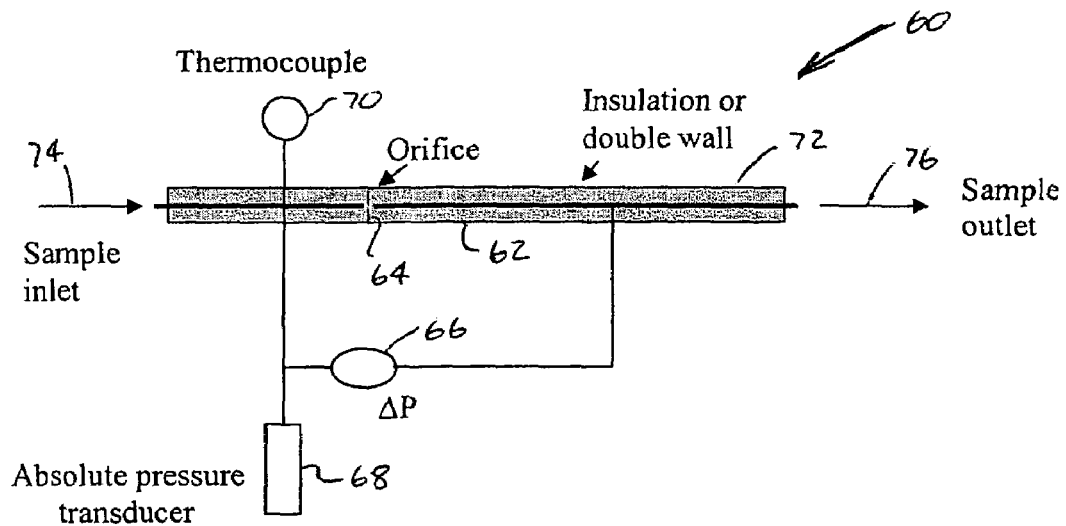
FIG. 2 illustrates a first embodiment of the orifice flow meter.
Figure 3:
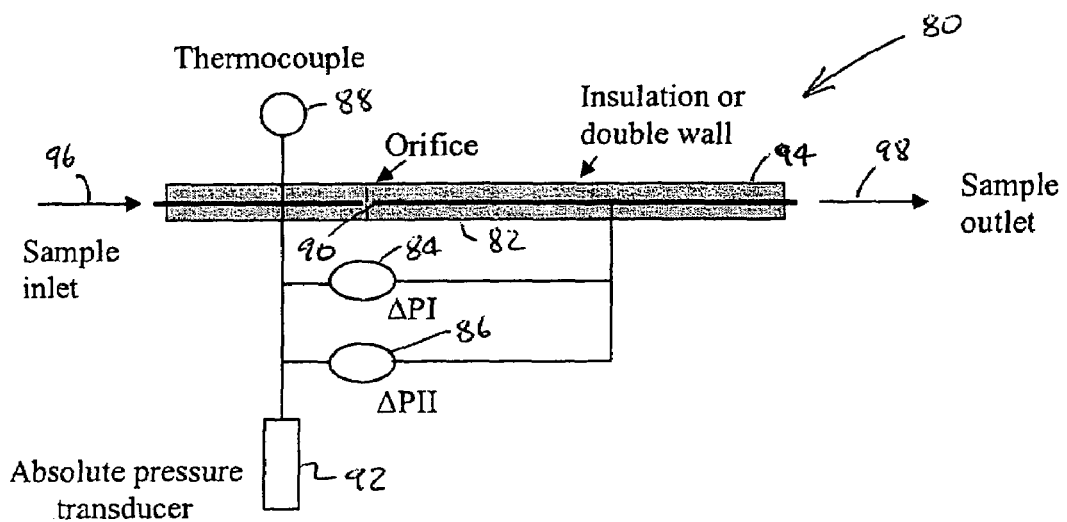
FIG. 3 illustrates a second embodiment of the orifice flow meter.
Figure 4:
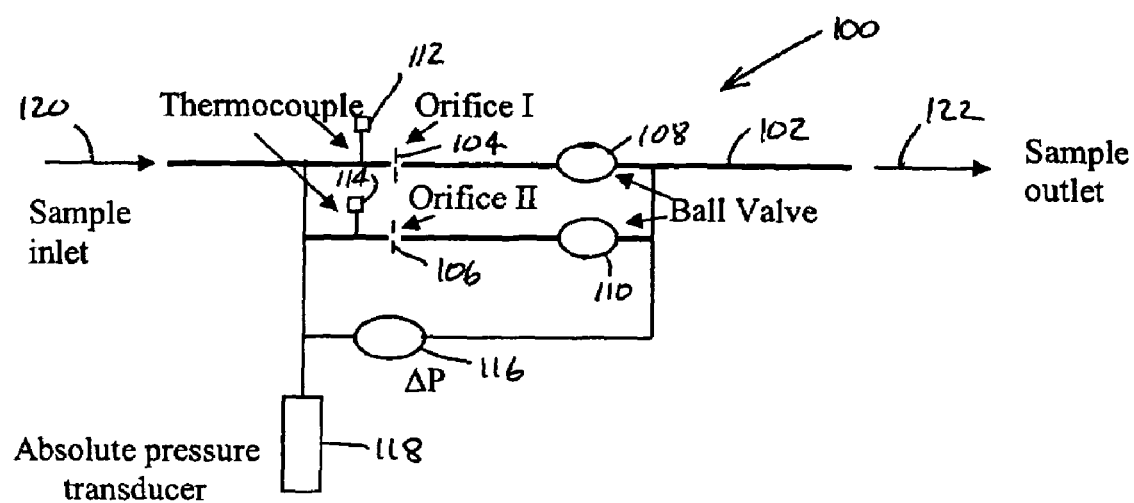
FIG. 4 illustrates a third embodiment of the orifice flow meter.

FIGS. 2-4 illustrate various embodiments of orifice flow meter 12. Other designs are possible for orifice flow meters. An appropriate orifice flow meter for the sampler depends on the application or specification of the sampler.

FIG. 2 illustrates an orifice flow meter 60 having flow meter body 62. Orifice flow meter 60 includes an orifice 64, a differential pressure transducer 66, an absolute pressure transducer 68, a thermocouple 70, insulation or double wall tubing 72, sample inlet 74 and sample outlet 76. The purpose of using insulation or double wall tubing is to minimize heat losses over orifice flow meter 60. Under some circumstances, the orifice flow meter 60 may be made without the insulation or double wall. In this embodiment, because there is only one orifice 64 and one differential pressure transducer 66, this orifice flow meter 60 is suitable for a sampler with small dilution ratio variation.

FIG. 3 illustrates an alternative orifice flow meter 80 having flow meter body 82. Orifice flow meter 80 includes first differential pressure transducer 84, second differential pressure transducer 86, thermocouple 88, orifice 90, absolute pressure transducer 92, insulation or double wall tubing 94, sample inlet 96 and sample outlet 98. The differential pressure transducers 84, 86 have different ranges. It is also possible to include additional differential pressure transducers.

Multiple calibration curves for flow rate are calibrated as a function of the pressure difference over the orifice 90 for each transducer 84, 86. The appropriate calibration curve and pressure transducer are selected based on the pressure difference over the orifice 90 and the ranges of the transducers 84, 86. The purpose of using insulation or double wall tubing is to minimize heat losses over the orifice flow meter 80. Under some circumstances, the orifice flow meter 80 can be made without the insulation or double wall. Orifice flow meter 80 may provide improved accuracy because multiple differential pressure transducers 84, 86 are included. Orifice flow meter 80 is suitable for a sampler requiring precise sample flow measurement.

FIG. 4 illustrates another alternative orifice flow meter 100 having flow meter body 102. Orifice flow meter 100 includes orifices 104, 106, ball valves 108, 110, thermocouples 112, 114, pressure transducer 116, absolute pressure transducer 118, sample inlet 120 and sample outlet 122. A calibration curve can be made for each orifice 104, 106. Since an orifice is sensitive to some range of sample flow, the accuracy of flow measurement may drop when the sample flow is beyond the range of the orifice. In orifice flow meter 100, the best orifice could be selected by opening the ball valve on the same flow loop. Since there is no restriction in the ball valve while it is open, the ball valve does not cause particle losses. The valves may be controlled manually or automatically. As a result, the most accurate flow measurement for the sample flow could be obtained in a wide range. This orifice flow meter 100 is suitable for a sampler which requires a wide range of dilution ratios or sample ratios.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A partial flow sampling system wherein a sample inlet probe and transfer line receive an exhaust sample flow, the system comprising:
    a system inlet for receiving the exhaust sample flow;
    a dilution air control system for selectively controlling a dilution air flow rate;
    a mixer receiving and mixing the exhaust sample flow and the dilution air flow to produce a mixture flow;
    a total flow control system for controlling the mixture flow rate; and
    an orifice flow meter installed at the system inlet for measuring the exhaust sample flow rate in real-time, thereby providing accurate sample flow measurements over a wide range of dilution ratios and sample ratios, wherein the dilution air control system selectively controls the dilution air flow rate based on either one or the other of
    (i) a desired dilution ratio and the measured exhaust sample flow rate to cause a system dilution ratio to track the desired dilution ratio, and
    (ii) a desired sample ratio and the measured exhaust sample flow rate to cause a system sample ratio to track the desired sample ratio.

2. The system of claim 1 further comprising:
    a control loop receiving a signal indicative of the measured exhaust sample flow rate and receiving a reference signal, the control loop producing a signal to drive the dilution air control system.

3. The system of claim 2 wherein the control loop includes a proportional, integral, derivative controller.

4. The system of claim 1 further comprising:
    an outlet port after the mixer to provide a sample to a particle instrument.

5. The system of claim 1 wherein the orifice flow meter includes a first orifice, a first differential pressure transducer, an absolute pressure transducer, and a first thermocouple.

6. The system of claim 5 wherein the orifice flow meter further includes a second differential pressure transducer.

7. A partial flow sampling system wherein a sample inlet probe and transfer line receive an exhaust sample flow, the system comprising:
    a system inlet for receiving the exhaust sample flow;
    a dilution air control system for controlling a dilution air flow rate;
    a mixer receiving and mixing the exhaust sample flow and the dilution air flow to produce a mixture flow;
    a total flow control system for controlling the mixture flow rate;
    a sample filter between the mixer and the total flow control system;
    a bypass filter between the mixer and the total flow control system, wherein flow through the bypass filter bypasses the sample filter; and
    an orifice flow meter installed at the system inlet for measuring the exhaust sample flow rate in real-time, thereby providing accurate sample flow measurements over a wide range of dilution ratios and sample ratios.

8. The system of claim 7 further comprising:
a first valve associated with and downstream of the sample filter; and
a second valve associated with and downstream of the bypass filter.

9. A partial flow sampling system wherein a sample inlet probe and transfer line receive an exhaust sample flow, the system comprising:
a system inlet for receiving the exhaust sample flow;
a dilution air control system for controlling a dilution air flow rate;
a mixer receiving and mixing the exhaust sample flow and the dilution air flow to produce a mixture flow;
a total flow control system for controlling the mixture flow rate; and
an orifice flow meter installed at the system inlet for measuring the exhaust sample flow rate in real-time wherein the orifice flow meter includes a first orifice, a first differential pressure transducer, an absolute pressure transducer, and a first thermocouple and wherein the orifice flow meter further includes a second orifice, a second thermocouple, a first valve associated with the first orifice, and a second valve associated with the second orifice, thereby providing accurate sample flow measurements over a wide range of dilution ratios and sample ratios.

10. A method of operating a partial flow sampling system wherein a sample inlet probe and transfer line receive an exhaust sample flow, the system including a system inlet for receiving the exhaust sample flow, a dilution air control system for controlling a dilution air flow rate, a mixer receiving and mixing the exhaust sample flow and the dilution air flow to produce a mixture flow, a total flow control system for controlling the mixture flow rate and an orifice flow meter installed at the system inlet for measuring the exhaust sample flow rate in real-time, thereby providing accurate sample flow measurements over a wide range of dilution ratios and sample ratios, the method comprising:
determining a desired dilution ratio;
driving the dilution air control system based on the desired dilution ratio and the measured exhaust sample flow rate to cause a system dilution ratio to track the desired dilution ratio.

* * * * *